US00PP20161P2

(12) United States Plant Patent
Dümmen

(10) Patent No.: US PP20,161 P2
(45) Date of Patent: Jul. 7, 2009

(54) ***GERANIUM* PLANT NAMED 'DUEVIHOTPI'**

(50) Latin Name: *Pelargonium×hortorum*
Varietal Denomination: DUEVIHOTPI

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/214,236

(22) Filed: Jun. 16, 2008

(51) Int. Cl.
*A01H 5/00* (2006.01)

(52) U.S. Cl. ..... Plt./325

(58) Field of Classification Search ..... Plt./328, Plt./325

See application file for complete search history.

*Primary Examiner*—Kent L Bell
(74) *Attorney, Agent, or Firm*—C. A. Whealy

(57) ABSTRACT

A new and distinct cultivar of Zonal *Geranium* plant named 'Duevihotpi', characterized by its upright to outwardly spreading plant habit; vigorous growth habit; freely basal branching habit; bright green-colored leaves; freely flowering habit; semi-double dark pink-colored flowers with red purple-colored central spots; and good garden performance.

1 Drawing Sheet

Botanical designation: *Pelargonium×hortorum*.
Cultivar denomination: 'Duevihotpi'.

BACKGROUND OF THE INVENTION

The present invention relates to a new and distinct cultivar of Zonal *Geranium*, botanically known as *Pelargonium×hortorum,* and hereinafter referred to by the name 'Duevihotpi'.

The new Zonal *Geranium* is a product of a planned breeding program conducted by the Inventor in Rheinberg, Germany. The objective of the breeding program is to create new vigorous Zonal *Geranium* cultivars with numerous attractive flowers.

The new Zonal *Geranium* originated from a cross-pollination made by the Inventor in May, 2002 in Rheinberg, Germany of a proprietary selection of *Pelargonium×hortorum* identified as code number Z98-2741-2, not patented, as the female, or seed, parent with a proprietary selection of *Pelargonium×hortorum* identified as code number Z98-3340-1, not patented, as the male, or pollen, parent. The new Zonal *Geranium* was discovered and selected by the Inventor as a flowering plant from within the progeny of the stated cross-pollination in a controlled greenhouse environment in Rheinberg, Germany in May, 2004.

Asexual reproduction of the new Zonal *Geranium* by vegetative terminal cuttings in a controlled greenhouse environment in Rheinberg, Germany since May, 2004, has shown that the unique features of this new Zonal *Geranium* are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duevihotpi'. These characteristics in combination distinguish 'Duevihotpi' as a new and distinct cultivar of Zonal *Geranium*:

1. Upright to outwardly spreading plant habit.
2. Vigorous growth habit.
3. Freely basal branching habit.
4. Bright green-colored leaves.
5. Freely flowering habit.
6. Semi-double dark pink-colored flowers with red purple-colored central spots.
7. Good garden performance.

Plants of the new Zonal *Geranium* differ primarily from plants of the female parent selection in flower color as plants of the female parent selection have purple-colored flowers. Additionally, plants of the new Zonal *Geranium* are more vigorous than plants of the female parent selection.

Plants of the new Zonal *Geranium* differ primarily from plants of the male parent selection in flower color as plants of the male parent selection have purple-colored flowers. Additionally, plants of the new Zonal *Geranium* are more vigorous than plants of the male parent selection.

Plants of the new Zonal *Geranium* can be compared to plants of *Pelargonium×hortorum* 'Melrose', not patented. In side-by-side comparisons conducted in Rheinberg, Germany, plants of the new Zonal *Geranium* differed from plants of 'Melrose' in the following characteristics:

1. Plants of the new Zonal *Geranium* were more vigorous than plants of 'Melrose'.
2. Plants of the new Zonal *Geranium* had larger leaves than 'Melrose'.
3. Plants of the new Zonal *Geranium* had larger flowers than plants of 'Melrose'.
4. Plants of the new Zonal *Geranium* had longer peduncles than plants of the 'Melrose'.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*. The photograph comprises a side perspective view of a typical flowering plant of 'Duevihotpi' grown in a container.

DETAILED BOTANICAL DESCRIPTION

The aforementioned photograph and following observations and measurements describe plants grown in Rheinberg, Germany in a glass-covered greenhouse during the summer and under conditions which closely approximate commercial production. During the production of the plants, day and night temperatures averaged 18° C. and light levels averaged 4,500 lux. Plants were pinched one time three weeks after planting. Plants were two months from planting when the photograph and the description were taken. In the detailed description, color references are made to The Royal Horticultural Society Colour Chart, 2001 Edition, except where general terms of ordinary dictionary significance are used.

Botanical classification: *Pelargonium×hortorum* 'Duevihotpi'.

Parentage:

*Female, or seed, parent.*—Proprietary selection of *Pelargonium×hortorum* identified as code number Z98-2741-2, not patented.

*Male or pollen parent.*—Proprietary selection of *Pelargonium×hortorum* identified as code number Z98-3340-1, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching.

Plant description:

*General appearance.*—Upright to outwardly spreading plant habit; uniformly rounded; densely foliated.

*Growth and branching habit.*—Vigorous growth habit. Freely basal branching habit with about three lateral branches developing per plant.

*Plant height.*—About 23 cm.

*Plant width.*—About 22 cm.

*Lateral branches.*—Length: About 6 cm. Diameter: About 2 mm. Internode length: About 1.2 cm. Texture: Slightly pubescent. Strength: Strong. Color: Close to 144A.

Foliage description:

*Arrangement.*—Alternate, simple.

*Length.*—About 9.2 cm.

*Width.*—About 12.1 cm.

*Shape.*—Reniform.

*Apex.*—Acute.

*Base.*—Cordate.

*Margin.*—Crenate.

*Venation pattern.*—Palmate.

*Texture, upper and lower surfaces.*—Pubescent.

*Color.*—Developing and fully expanded foliage, upper surface: Close to 137B; venation, close to 144A. Developing and fully expanded foliage, lower surface: Close to 138B; venation, close to 144A. Zonation pattern: Not observed.

*Petiole.*—Length: About 9.9 cm. Diameter: About 3 mm. Texture, upper and lower surfaces: Smooth, glabrous. Color, upper and lower surfaces: Close to 144A.

Flower description:

*Flower arrangement.*—Semi-double rotate flowers arranged in rounded hemispherical umbels arising from apical leaf axils. Umbels displayed above the foliage on moderately strong peduncles. Flowers face upright to outward.

*Fragrance.*—Note detected.

*Quantity of flowers.*—Freely flowering habit; about 20 to 25 flowers per umbel.

*Flowering season.*—Year-round under greenhouse conditions. In Germany, flowering is continuous from spring throughout the summer. Flowers persistent.

*Flower longevity.*—Individual flowers last about five to seven days on the plant.

*Umbel height.*—About 5.5 cm.

*Umbel diameter.*—About 10.5 cm.

*Flower diameter.*—About 5 cm.

*Flower depth (height).*—About 2 cm.

*Flower buds.*—Length: About 1.3 cm. Diameter: About 8.7 mm. Shape: Ovoid. Color: Close to 144A.

*Petals.*—Quantity per flower: About five or six. Length: About 2.7 cm. Width: About 2.5 cm. Shape: Obovate. Apex: Rounded. Base: Attenuate. Margin: Sinuate. Aspect: Mostly flat. Texture, upper and lower surfaces: Smooth, glabrous. Color: When opening and fully opened, upper surface: Close to 66A; central spot, close to 61B. When opening and fully opened, lower surface: Close to 66C to 66D.

*Petaloids.*—Quantity per flower: About three. Length: About 2.7 cm. Width: About 4.1 cm. Shape: Obovate. Apex: Rounded. Base: Attenuate. Margin: Sinuate. Texture, upper and lower surfaces: Smooth, glabrous. Color: When opening and fully opened, upper surface: Close to 66A; central spot, close to 61B. When opening and fully opened, lower surface: Close to 66C to 66D.

*Sepals.*—Quantity per flower: Five, arranged in a single whorl. Length: About 1.1 cm. Width: About 3.8 mm. Shape: Lanceolate. Apex: Apiculate. Base: Attenuate. Margin: Entire. Color, upper and lower surfaces: Close to 144A.

*Peduncle (umbel stem).*—Length: About 15.8 cm. Diameter: About 2 mm to 4 mm. Strength: Moderately strong. Texture: Smooth, glabrous. Color: Close to 144A.

*Pedicel (individual flower stem).*—Length: About 2.3 cm. Diameter: About 1 mm to 2 mm. Strength: Moderately strong. Texture: Pubescent. Color: Close to 144A tinted with close to 59A.

*Reproductive organs.*—Androecium: Stamen quantity per flower: About ten. Anther length: About 2 mm. Anther shape: Oval. Anther color: Close to 34A. Pollen amount: Moderate. Pollen color: Close to 28A.

Gynoecium: Pistil quantity per flower: One. Pistil length: About 9 mm. Stigma shape: Parted. Stigma color: Close to 61A. Style length: About 2 mm. Style color: Close to 61A.

*Seed/fruit.*—Seed and fruit development have not been observed.

Disease/pest resistance: Plants of the new Zonal *Geranium* have not been observed to be resistant to pathogens and pests common to Zonal *Geranium*.

Garden performance: Plants of the new Zonal *Geranium* have been observed to tolerate rain, wind, and temperatures ranging from about 5° C. to about 40° C. and have demonstrated good garden performance.

It is claimed:

1. A new and distinct Zonal *Geranium* plant named 'Duevihotpi' as illustrated and described.

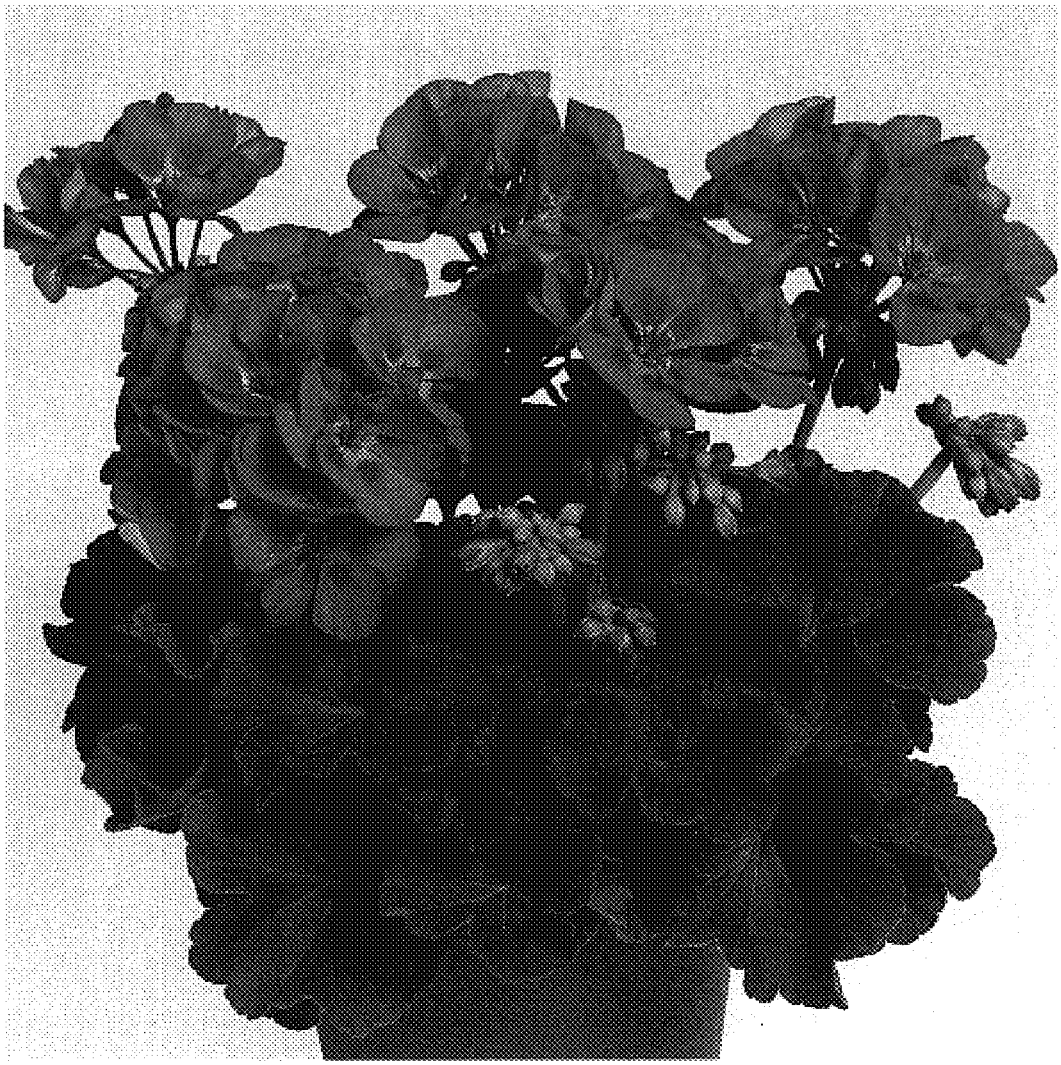

* * * * *